(12) United States Patent
Kuwabara

(10) Patent No.: US 11,154,265 B2
(45) Date of Patent: Oct. 26, 2021

(54) RADIOGRAPHIC IMAGE CAPTURING SYSTEM, CONTROL DEVICE, CONTROL METHOD, AND CONTROL PROGRAM

(71) Applicant: FUJIFILM CORPORATION, Tokyo (JP)

(72) Inventor: Takao Kuwabara, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 84 days.

(21) Appl. No.: 16/749,978

(22) Filed: Jan. 22, 2020

(65) Prior Publication Data

US 2020/0155100 A1   May 21, 2020

Related U.S. Application Data

(63) Continuation of application No. PCT/JP2018/028327, filed on Jul. 27, 2018.

(30) Foreign Application Priority Data

Jul. 27, 2017   (JP) .............................. JP2017-145848

(51) Int. Cl.
*A61B 6/00*   (2006.01)
*A61B 6/04*   (2006.01)

(52) U.S. Cl.
CPC ............ *A61B 6/502* (2013.01); *A61B 6/0414* (2013.01); *A61B 6/42* (2013.01); *A61B 6/54* (2013.01)

(58) Field of Classification Search
CPC ......... A61B 6/481; A61B 6/502; A61B 6/461; A61B 6/12; A61B 6/42; A61B 6/54; A61B 6/0414
See application file for complete search history.

(56) References Cited

U.S. PATENT DOCUMENTS

2016/0183896 A1* 6/2016 Muller .................. A61B 6/461
                                                                                600/424
2017/0079601 A1    3/2017 Hoernig et al.

FOREIGN PATENT DOCUMENTS

JP      2002-263088 A    9/2002
JP      2008-284055 A   11/2008
(Continued)

OTHER PUBLICATIONS

"Vehicle-mounted X-ray breast imaging system: MGU-1000D type MAMMOREX Pe-ru-ru DIGITAL", Toshiba Medical Systems Corporation, Jun. 7, 2012 (1st edition ), internet :<http://www.info.pmda.go.jp/downfiles/md/PDF/480123/480123_224ABBZX00101000_A01_01.pdf>.

(Continued)

*Primary Examiner* — Don K Wong
(74) *Attorney, Agent, or Firm* — Solaris Intellectual Property Group, PLLC

(57) ABSTRACT

A radiographic image capturing system including (i) an instruction unit, (ii) a mammography apparatus that performs contrast imaging so as to compress a breast, by a compression plate, and to continuously execute first imaging, in which a first radiographic image is generated, and second imaging, in which radiation a second radiographic image is generated, and (iii) a controller that performs control to have the mammography apparatus perform the contrast imaging in a case in which an instruction signal is inputted into, and a period during which outputting of the instruction signal is stopped does not exceed a predetermined time, and to display information indicating a predetermined warning on a display unit prior to an interruption of contrast imaging, in a case in which the instruction signal is stopped before the second imaging is completed after start of the first imaging.

12 Claims, 12 Drawing Sheets

(56) References Cited

FOREIGN PATENT DOCUMENTS

| | | |
|---|---|---|
| JP | 2011-152197 A | 8/2011 |
| JP | 2012-501750 A | 1/2012 |
| JP | 2014-76290 A | 5/2014 |
| WO | 2010/028208 A1 | 3/2010 |

OTHER PUBLICATIONS

International Search Report issued in International Application No. PCT/JP2018/028327 dated Oct. 2, 2018.
Written Opinion of the ISA issued in International Application No. PCT/JP2018/028327 dated Oct. 2, 2018.
English language translation of the following: Office action dated Aug. 11, 2020 from the JPO in a Japanese patent application No. 2019-532889 corresponding to the instant patent application.
Extended European Search Report dated Jun. 9, 2020, issued in corresponding EP Patent Application No. 18837732.9.

\* cited by examiner

RADIOGRAPHIC IMAGE CAPTURING SYSTEM, CONTROL DEVICE, CONTROL METHOD, AND CONTROL PROGRAM

CROSS-REFERENCE TO RELATED APPLICATION

This application is a continuation application of International Application No. PCT/JP2018/028327, filed Jul. 27, 2018, the disclosure of which is incorporated herein by reference in its entirety. Further, this application claims priority from Japanese Patent Application No. 2017-145848 filed Jul. 27, 2017, the disclosure of which is incorporated herein by reference in their entirety.

BACKGROUND OF THE INVENTION

1. Field of the Invention

The present invention relates to a radiographic image capturing system, a control device, a control method, and a control program.

2. Description of the Related Art

A mammography apparatus is known that captures a radiographic image by emitting radiation from a radiation source toward the breast of a subject and detecting radiation transmitted through the breast using a radiation detector.

In general, a mammography apparatus captures a radiographic image by emitting radiation from a radiation source to a breast in a case where an instruction unit, such as a button or a switch for giving an instruction to emit radiation, is pressed by a user such as a technician. In this type of mammography apparatus, for example, as disclosed in JP2011-152197A, radiographic image capturing is interrupted in a case where the user releases his/her hand from the instruction unit so that the pressing of the instruction unit is released.

SUMMARY OF THE INVENTION

Incidentally, as a mammography apparatus, there is known a mammography apparatus that performs contrast imaging for continuously performing first imaging, in which radiation having a first energy is emitted to a breast with a contrast medium administered thereto and a first radiographic image is generated by a radiation detector, and second imaging, in which radiation having a second energy different from the first energy is emitted and a second radiographic image is generated by the radiation detector.

In the case of performing imaging multiple times continuously as described above, for example, in the technique described in JP2011-152197A, in a case where the user stops pressing the instruction unit between imaging and imaging, the imaging may be interrupted before the entire imaging is completed. In the case of the above contrast imaging, for example, in a case where the user stops pressing the instruction unit between the first imaging and the second imaging, the contrast imaging may be interrupted before the second imaging is completed.

In a case where the imaging is interrupted on the way, the imaging should be performed again. Since it may be necessary to redo all the continuous imaging from the beginning, this may put a burden on the subject.

The present disclosure has been made in consideration of the above circumstances, and provides a radiographic image capturing system, a control device, a control method, and a control program capable of reducing the burden on a subject in contrast imaging.

A radiographic image capturing system of a first aspect of the present disclosure comprises: an instruction unit that outputs an instruction signal in response to a user operation; a mammography apparatus that performs contrast imaging in which a breast in a state in which a contrast medium is administered is compressed by a compression plate and first imaging, in which radiation having a first energy is emitted from a radiation source to the breast according to the instruction signal and a first radiographic image is generated by a radiation detector, and second imaging, in which radiation having a second energy different from the first energy is emitted from the radiation source to the breast and a second radiographic image is generated by the radiation detector, are continuously performed; and a controller that performs control to display information indicating a predetermined warning on a display unit in a case where the instruction signal is stopped before the second imaging is completed after start of the first imaging.

The controller of the radiographic image capturing system of a second aspect of the present disclosure interrupts the contrast imaging of the mammography apparatus in a case where the stop of the instruction signal is maintained after a predetermined time has passed after displaying the information indicating the warning on the display unit.

The mammography apparatus of the radiographic image capturing system of a third aspect of the present disclosure releases compression of the breast by the compression plate in a case of interrupting the contrast imaging.

The information indicating the warning in the radiographic image capturing system of a fourth aspect of the present disclosure includes information indicating a remaining time until the contrast imaging is interrupted.

The radiographic image capturing system of a fifth aspect of the present disclosure further comprises a reception unit that receives an instruction to interrupt the contrast imaging, and the controller interrupts the contrast imaging of the mammography apparatus in a case where the reception unit receives the interruption instruction.

The controller of the radiographic image capturing system of a sixth aspect of the present disclosure causes the contrast imaging of the mammography apparatus to continue in a case where the instruction signal is output again from the instruction unit before the predetermined time passes after the instruction signal is stopped.

The information indicating the warning in the radiographic image capturing system of a seventh aspect of the present disclosure includes information indicating that the contrast imaging is interrupted.

The controller of the radiographic image capturing system of an eighth aspect of the present disclosure displays information indicating that the contrast imaging is being performed on the display unit until the contrast imaging of the mammography apparatus is completed or interrupted from start of the contrast imaging.

The controller of the radiographic image capturing system of a ninth aspect of the present disclosure displays information indicating completion of the contrast imaging on the display unit in a case where the contrast imaging is completed.

A control device of a tenth aspect of the present disclosure is a control device that controls a mammography apparatus that performs contrast imaging in which a breast in a state in which a contrast medium is administered is compressed by a compression plate and first imaging, in which radiation having a first energy is emitted from a radiation source to the breast according to an instruction signal output from an instruction unit in response to a user operation and a first radiographic image is generated by a radiation detector, and second imaging, in which radiation having a second energy different from the first energy is emitted from the radiation source to the breast and a second radiographic image is generated by the radiation detector, are continuously performed. The control device comprises: a determination unit that determines whether or not the instruction signal has been stopped before the second imaging is completed after start of the first imaging; and a controller that performs control to display information indicating a predetermined warning on a display unit in a case where the determination unit determines that the instruction signal has been stopped.

A control method of an eleventh aspect of the present disclosure is a control method for a mammography apparatus that performs contrast imaging in which a breast in a state in which a contrast medium is administered is compressed by a compression plate and first imaging, in which radiation having a first energy is emitted from a radiation source to the breast according to an instruction signal output from an instruction unit in response to a user operation and a first radiographic image is generated by a radiation detector, and second imaging, in which radiation having a second energy different from the first energy is emitted from the radiation source to the breast and a second radiographic image is generated by the radiation detector, are continuously performed. The method comprises: processing for determining whether or not the instruction signal has been stopped before the second imaging is completed after start of the first imaging; and processing for performing control to display information indicating a predetermined warning on a display unit in a case where it is determined that the instruction signal has been stopped.

A control program of a twelfth aspect of the present disclosure is a control program causing a computer to control a mammography apparatus that performs contrast imaging in which a breast in a state in which a contrast medium is administered is compressed by a compression plate and first imaging, in which radiation having a first energy is emitted from a radiation source to the breast according to the instruction signal and a first radiographic image is generated by a radiation detector, and second imaging, in which radiation having a second energy different from the first energy is emitted from the radiation source to the breast and a second radiographic image is generated by the radiation detector, are continuously performed. The program causes the computer to execute: processing for determining whether or not the instruction signal has been stopped before the second imaging is completed after start of the first imaging; and processing for performing control to display information indicating a predetermined warning on a display unit in a case where it is determined that the instruction signal has been stopped.

The control device of the present disclosure is a control device having a processor. The processor is a processor that controls a mammography apparatus that performs contrast imaging in which a breast in a state in which a contrast medium is administered is compressed by a compression plate and first imaging, in which radiation having a first energy is emitted from a radiation source to the breast according to an instruction signal output from an instruction unit in response to a user operation and a first radiographic image is generated by a radiation detector, and second imaging, in which radiation having a second energy different from the first energy is emitted from the radiation source to the breast and a second radiographic image is generated by the radiation detector, are continuously performed. The processor determines whether or not the instruction signal has been stopped before the second imaging is completed after start of the first imaging, and displays information indicating a predetermined warning on a display unit in a case where it is determined that the instruction signal has been stopped.

According to the present disclosure, it is possible to reduce the burden on the subject in contrast imaging.

DESCRIPTION OF THE PREFERRED EMBODIMENTS

Hereinafter, embodiments of the present invention will be described in detail with reference to the accompanying diagrams. In addition, the present embodiment does not limit the present invention.

First Embodiment

Figure 1:
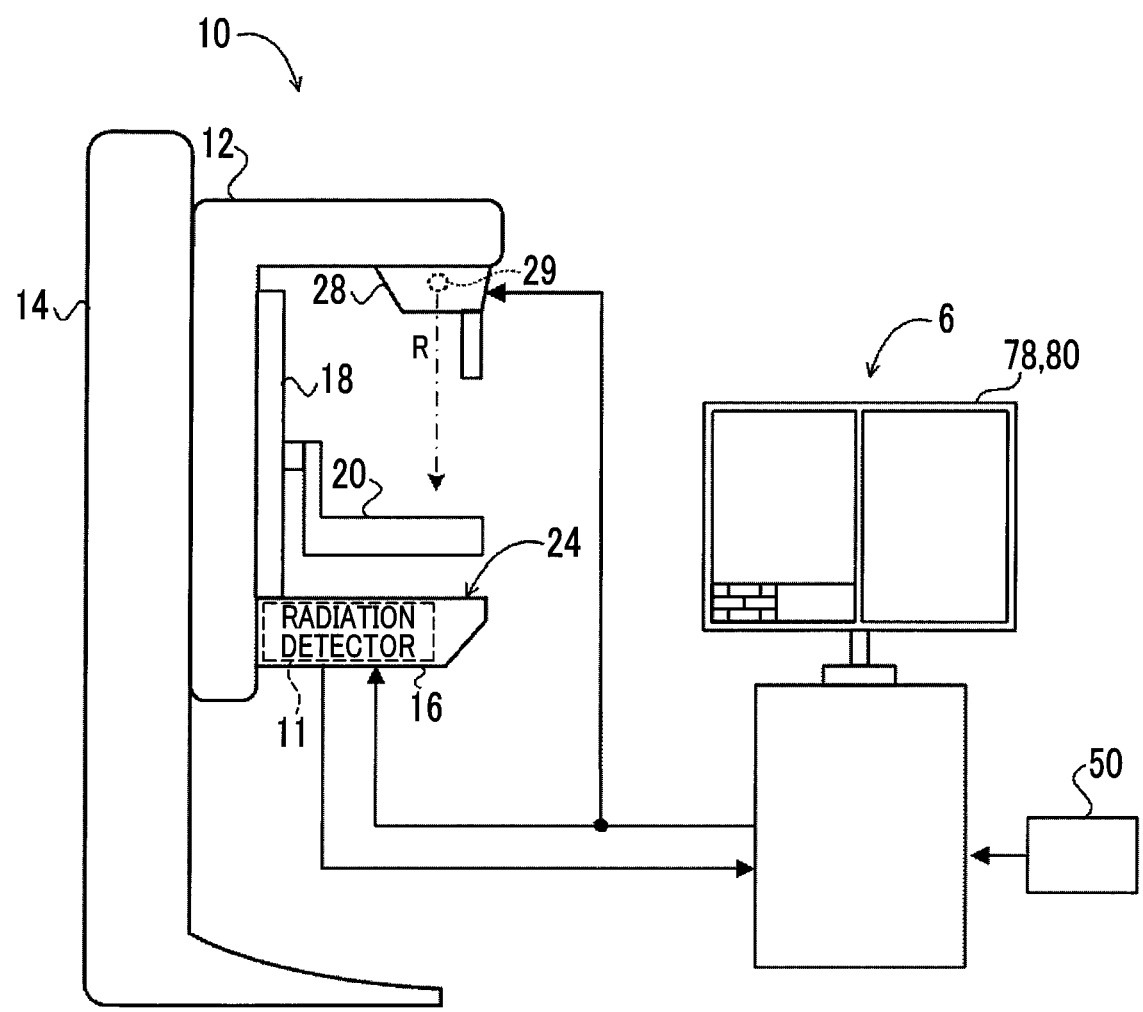
FIG. 1 is a configuration diagram schematically showing an example of the overall configuration of a radiographic image capturing system of a first embodiment.

First, an example of the overall configuration of a radiographic image capturing system of the present embodiment will be described. In FIG. 1, a block diagram showing an example of the overall configuration of a radiographic image capturing system 1 of the present embodiment is shown.

The radiographic image capturing system 1 of the present embodiment has a function of capturing a radiographic image by the operation of a user, such as a doctor or a radiology technician, based on an instruction (imaging order) input from an external system (for example, a radiology information system (RIS)) through the console 6.

Figure 2:
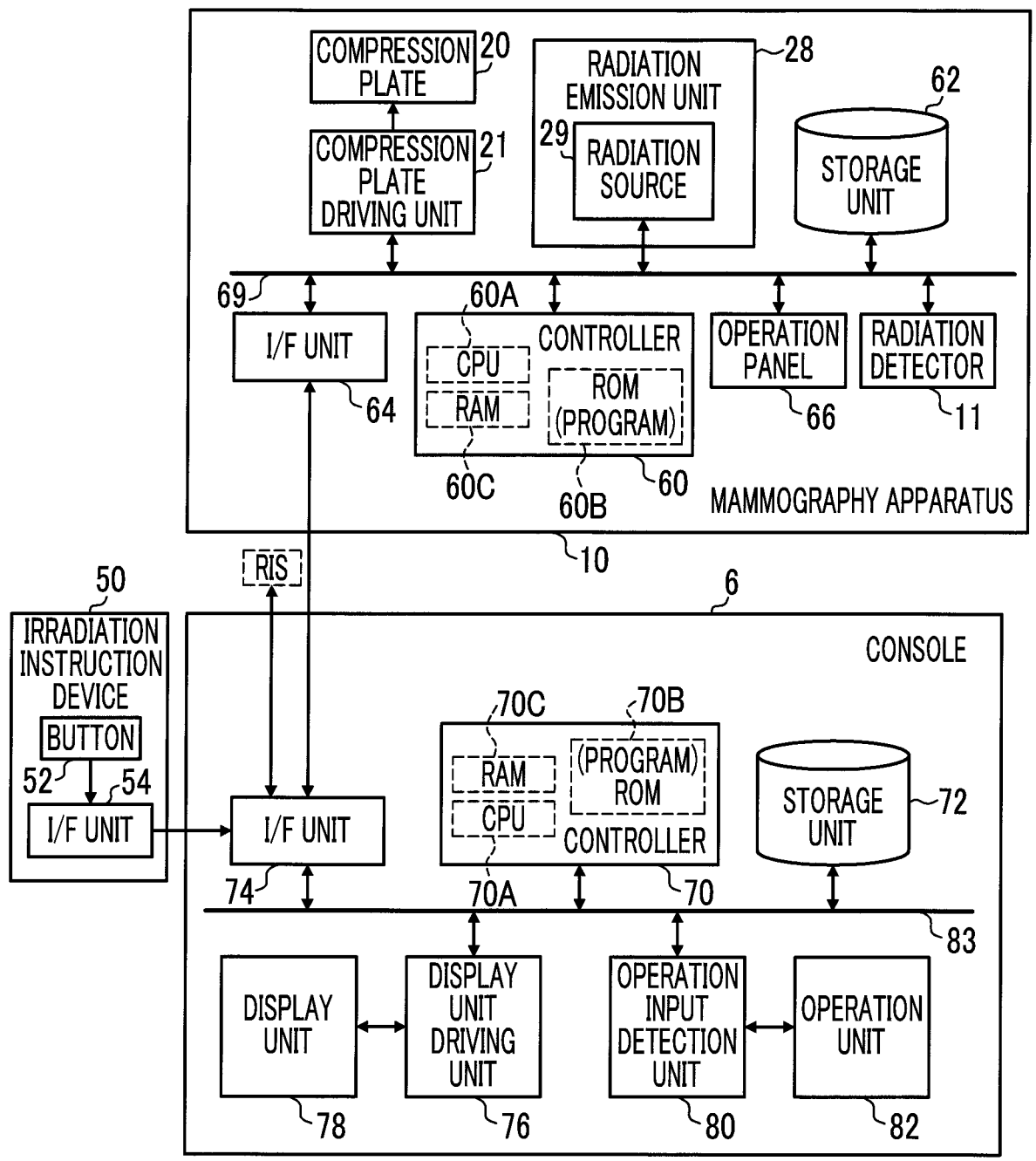
FIG. 2 is a block diagram showing an example of the configuration of a console, a mammography apparatus, and an irradiation instruction device of the first embodiment.

As shown in FIG. 1, the radiographic image capturing system 1 of the present embodiment comprises a console 6, a mammography apparatus 10, and an irradiation instruction device 50. In FIG. 2, a block diagram showing an example of the configuration of the console 6, the mammography apparatus 10, and the irradiation instruction device 50 of the present embodiment is shown.

The mammography apparatus 10 of the present embodiment is an apparatus that captures a radiographic image of a breast by emitting radiation R (for example, X-rays) to the breast of the subject. In addition, the mammography apparatus 10 may be an apparatus that images the breast of the subject not only in a state in which the subject is standing (standing state) but also in a state in which the subject is sitting on a chair (including a wheelchair) or the like (sitting state), and may be any apparatus capable of capturing at least a radiographic image of the breast of the subject.

In addition, the mammography apparatus 10 of the present embodiment has a contrast enhanced digital mammography (CEDM) function for performing contrast imaging by energy subtraction imaging as a function of performing imaging in a state in which a contrast medium is administered to the breast of the subject, so-called contrast imaging.

As shown in FIG. 2, the mammography apparatus 10 of the present embodiment comprises a radiation detector 11, a compression plate driving unit 21 that drives a compression plate 20, a radiation emission unit 28 having a radiation source 29, a controller 60, a storage unit 62, an interface (I/F) unit 64, and an operation panel 66. The radiation detector 11, the compression plate driving unit 21, the radiation emission unit 28, the controller 60, the storage unit 62, the I/F unit 64, and the operation panel 66 are connected to each other through a bus 69, such as a system bus or a control bus, so that various kinds of information can be transmitted and received therebetween.

The controller 60 of the present embodiment controls the overall operation of the mammography apparatus 10 according to the control (instruction) of the console 6. The controller 60 comprises a central processing unit (CPU) 60A, a read only memory (ROM) 60B, and a random access memory (RAM) 60C. Various programs including a contrast imaging processing program to be described later, which are executed by the CPU 60A, are stored in advance in the ROM 60B. The RAM 60C temporarily stores various kinds of data.

Image data of a radiographic image captured by the radiation detector 11, other various kinds of information, and the like are stored in the storage unit 62. As specific examples of the storage unit 62, a hard disk drive (HDD), a solid state drive (SSD), and the like can be mentioned. The I/F unit 64 communicates with the console 6 by wireless communication or wired communication to transmit and receive various kinds of information therebetween. The operation panel 66 is provided as a plurality of switches on an imaging table 16 of the mammography apparatus 10, for example. In addition, the operation panel 66 may be provided as a touch panel.

Figure 3:
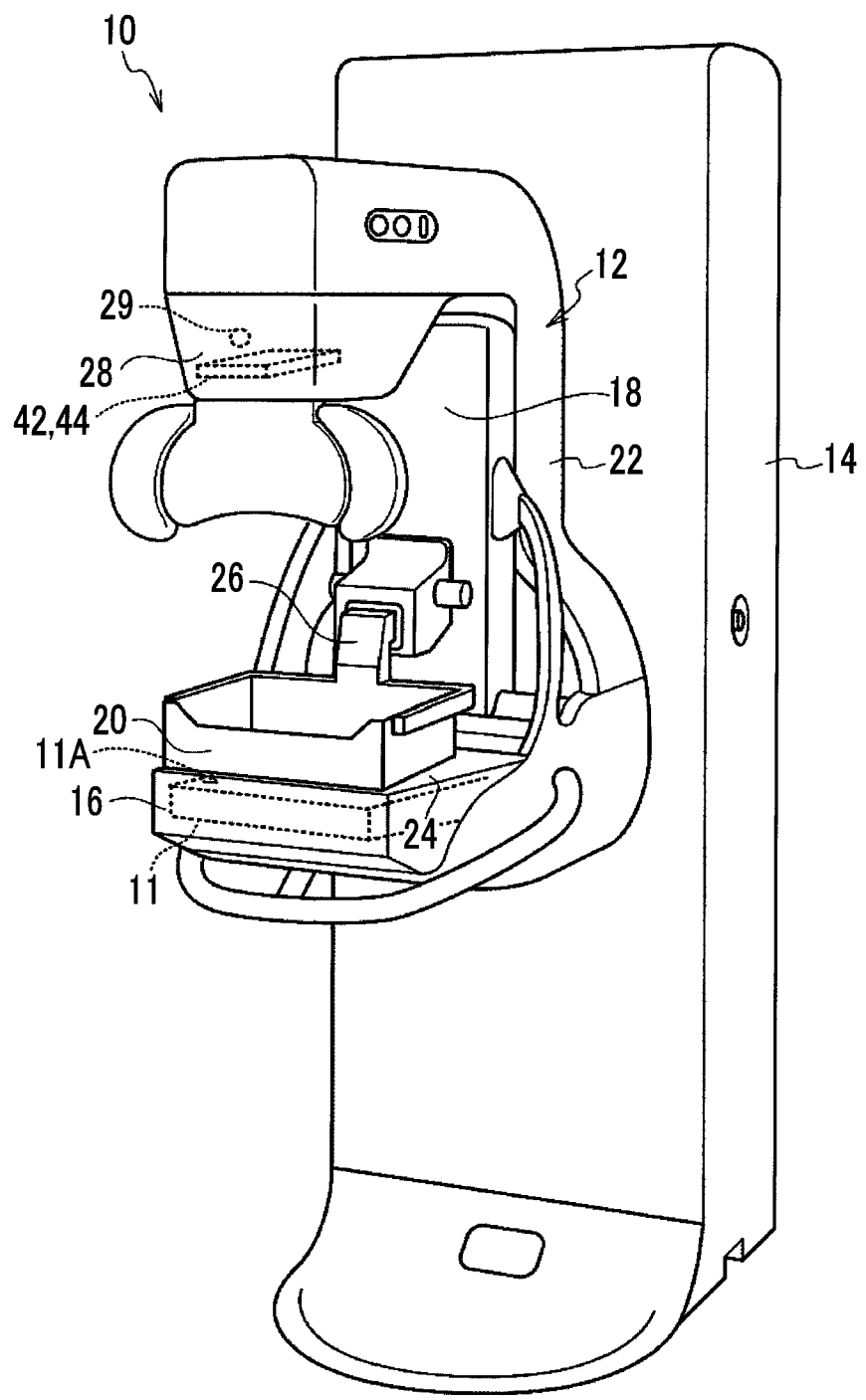
FIG. 3 is a perspective view in a case where an example of the overall configuration of the mammography apparatus of the first embodiment is viewed from the chest wall side of a subject.

In FIG. 3, a configuration diagram showing an example of the overall configuration of the mammography apparatus 10 of the present embodiment is shown. The following description will be given on the assumption that the side closer to the subject (chest wall side) in a case where the subject faces the mammography apparatus 10 in radiographic image capturing is the front side of the mammography apparatus 10 and the side away from the subject is the rear side of the mammography apparatus 10. In addition, the description will be given on the assumption that the left-right direction of the subject in a case where the subject faces the mammography apparatus 10 is the left-right direction of the mammography apparatus 10. In addition, the description will be given on the assumption that the head direction of the subject in a case where the subject faces the mammography apparatus 10 is the upper side and the foot direction is the lower side.

As shown in FIG. 3, the mammography apparatus 10 comprises an imaging unit 12, which has an approximately C shape in a side view and is provided on the front side of the apparatus, and a base unit 14 that supports the imaging unit 12 from the rear side of the apparatus.

The imaging unit 12 comprises the imaging table 16 having a planar imaging surface 24 in contact with the breast of the subject, the compression plate 20 for compressing the breast interposed between the compression plate 20 and the imaging surface 24 of the imaging table 16, and a holding unit 18 that supports the imaging table 16 and the compression plate 20. A member that transmits the radiation R is used as the compression plate 20. The imaging unit 12 comprises a support unit 22 that supports the radiation source 29 and the radiation emission unit 28, and the support unit 22 is separated from the holding unit 18.

As shown in FIG. 3, the radiation source 29 comprising a tube (tungsten as an example in the present embodiment) for emitting the radiation R to the breast is provided inside the radiation emission unit 28 of the mammography apparatus 10 of the present embodiment. In the radiation emission unit 28, a rhodium (Rh) filter 42 and a copper (Cu) filter 44 are provided between the radiation source 29 and the imaging table 16. In FIG. 3, the Rh filter 42 and the Cu filter 44 are shown as being integrated, but the filters are provided as separate filters.

The filters provided in the mammography apparatus 10 are not limited to the Rh filter 42 and the Cu filter 44. For example, a molybdenum (Mo) filter may be provided instead of the Rh filter 42 or in addition to the Rh filter 42. In addition, for example, an aluminum (Al) filter has a lower radiation R attenuation rate than the Rh filter 42. Therefore, the Al filter is suitable for tomosynthesis imaging in which the imaging time (radiation R emission time) at each imaging position in a state in which the radiation source 29 is continuously moved is short. For this reason, in a case where the mammography apparatus 10 has a function of performing tomosynthesis imaging, an Al filter may be provided and tomosynthesis imaging may be performed using the Al filter.

A moving unit (not shown) is provided inside the radiation emission unit 28. In the case of capturing a radiographic image, the Rh filter 42 or the Cu filter 44 is moved to a position in the irradiation field according to the energy of the radiation R to be emitted.

On the other hand, a shaft (not shown) is provided in the imaging unit 12 of the present embodiment, so that the imaging unit 12 can rotate with respect to the base unit 14.

The shaft is fixed to the support unit 22, so that the shaft and the support unit 22 rotate together. A gear is provided in each of the holding unit 18 and the shaft provided in the imaging unit 12. By switching the engagement state and the non-engagement state of the gears, it is possible to perform switching between a state in which the holding unit 18 and the shaft are connected to each other to rotate together and a state in which the shaft is separated from the holding unit 18 and idles. In addition, switching between transmission and non-transmission of the power of the shaft is not limited to the gear, and various mechanical elements can be used.

The holding unit 18 supports the imaging table 16 and the radiation source 29 by separating the imaging surface 24 and the radiation source 29 from each other by a predetermined distance. In addition, the holding unit 18 also holds the compression plate 20 through a support arm 26. The compression plate driving unit 21 (refer to FIG. 3) makes the support arm 26 of the holding unit 18 slide so that the compression plate 20 moves, and accordingly, the distance between the compression plate 20 and the imaging surface 24 changes.

The imaging surface 24 with which the breast of the subject comes into contact is formed of, for example, carbon from the viewpoint of radiolucency or strength. The radiation detector 11 that detects the radiation R transmitted through the breast and the imaging surface 24 is disposed in the imaging table 16. A radiographic image is generated based on the radiation R detected by the radiation detector 11. The type of the radiation detector 11 is not particularly limited. For example, an indirect conversion type radiation detector that converts the radiation R into light and converts the converted light into electric charge may be used, or a direct conversion type radiation detector that converts the radiation R into electric charge may be used. In the present embodiment, image data indicating a radiographic image output from the radiation detector 11 of the mammography apparatus 10 is transmitted to the console 6.

As described above, the mammography apparatus 10 of the present embodiment has a function of performing contrast imaging. As a contrast medium used for contrast imaging, a contrast medium using iodine having a k absorption edge of 33 keV (hereinafter, simply referred to as a "contrast medium") is generally used. The mammography apparatus 10 captures a first radiographic image with the radiation detector 11 by emitting the radiation R having a first energy lower than the k absorption edge of the contrast medium to the breast as a subject to which the contrast medium has been administered, and captures a second radiographic image with the radiation detector 11 by emitting the radiation R having a second energy higher than the k absorption edge of the contrast medium to the breast as a subject to which the contrast medium has been administered. The specific first energy and second energy are determined from the viewpoint of the specifications of the mammography apparatus 10, the desired image quality of the radiographic image, exposure of the subject, and the like in addition to the k absorption edge of the contrast medium. In general, the specific first energy and second energy are preferably 22 keV to 49 keV.

In the mammography apparatus 10 of the present embodiment, emitting the radiation R having the first energy refers to emitting the radiation R from the radiation source 29 by applying a tube voltage corresponding to the first energy. Similarly, emitting the radiation R having the second energy refers to emitting the radiation R from the radiation source 29 by applying a tube voltage corresponding to the second energy.

In the mammography apparatus 10 of the present embodiment, the first energy is the same as the energy of the radiation R used for normal (general) imaging. In the mammography apparatus 10, in the case of performing imaging by emitting the radiation R having the first energy (hereinafter, referred to as "LE imaging"), the Rh filter 42 is disposed in the irradiation field. Since the k absorption edge of Rh is 23.2 keV, the quality of the radiation R emitted to the subject is a radiation quality in which an energy component of 23.2 keV or more is suppressed. The LE imaging of the present embodiment is an example of first imaging of the present disclosure.

In the mammography apparatus 10 of the present embodiment, the second energy is set in the range of 45 keV to 49 keV. In the mammography apparatus 10, in the case of performing imaging by emitting the radiation R having the second energy (hereinafter, referred to as "HE imaging"), the Cu filter 44 is disposed in the irradiation field. The k absorption edge of Cu is 9.0 keV. The HE imaging of the present embodiment is an example of second imaging of the present disclosure.

The first radiographic image captured by the first imaging and the second radiographic image captured by the second imaging are output to the console 6.

The console 6 of the present embodiment has a function of controlling the mammography apparatus 10 using the imaging order or various kinds of information acquired from an external system or the like through a wireless communication local area network (LAN) or the like, an instruction signal output from the irradiation instruction device 50, and the like.

The console 6 of the present embodiment is a server computer as an example. As shown in FIG. 2, the console 6 comprises a controller 70, a storage unit 72, an I/F unit 74, a display unit driving unit 76, a display unit 78, an operation input detection unit 80, and an operation unit 82. The controller 70, the storage unit 72, the I/F unit 74, the display unit driving unit 76, and the operation input detection unit 80 are connected to each other through a bus 83, such as a system bus or a control bus, so that various kinds of information can be transmitted and received therebetween. The console 6 of the present embodiment is an example of a control device of the present disclosure.

The controller 70 of the present embodiment controls the overall operation of the console 6. The controller 70 comprises a CPU 70A, a ROM 70B, and a RAM 70C. Various programs including a control processing program to be described later, which are executed by the CPU 70A, are stored in advance in the ROM 70B. The RAM 70C temporarily stores various kinds of data.

Image data of a radiographic image captured by the mammography apparatus 10, other various kinds of information, and the like are stored in the storage unit 72. As specific examples of the storage unit 72, an HDD, an SSD, and the like can be mentioned.

The display unit 78 displays various kinds of information. The display unit driving unit 76 controls display of various kinds of information on the display unit 78. The operation unit 82 is used by the user to input various kinds of information, instructions regarding radiographic image capturing including a radiation R exposure instruction, and the like. The operation unit 82 is not particularly limited, and examples thereof include various switches, a touch panel, a touch pen, and a mouse. In addition, the operation unit 82 and the display unit 78 may be integrated to form a touch panel display. The operation input detection unit 80 detects an operation state with respect to the operation unit 82.

The I/F unit 74 communicates with an external system, such as the mammography apparatus 10 or the RIS, by wireless communication or wired communication to transmit and receive various kinds of information therebetween.

In addition, the console 6 receives an irradiation instruction signal from an I/F unit 54 of the irradiation instruction device 50 by wireless communication or wired communication through the I/F unit 74.

Figure 4:
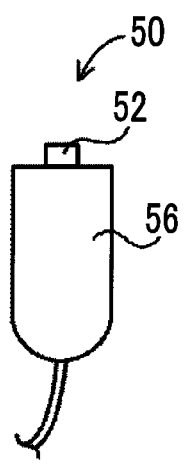
FIG. 4 is a diagram showing an example of the shape of the irradiation instruction device of the first embodiment.

The irradiation instruction device 50 comprises a button 52 and the I/F unit 54. The shape and the like of the irradiation instruction device 50 are not particularly limited. In the present embodiment, however, as in an example shown in FIG. 4, the irradiation instruction device 50 has a shape in which the button 52 is provided at one end of a gripping unit 56 gripped by the user. In a case where the user gives an instruction to emit the radiation R, the button 52 is pressed. In a case where the button 52 is pressed, an irradiation instruction signal is output to the console 6 through the I/F unit 54. The irradiation instruction device 50 of the present embodiment is an example of an instruction unit of the present disclosure, and the irradiation instruction signal of the present embodiment is an example of an instruction signal of the present disclosure.

In addition, the console 6 of the present embodiment receives image data of each of the first radiographic image and the second radiographic image from the mammography apparatus 10 by wireless communication or wired communication through the I/F unit 74.

The console 6 calculates the concentration distribution of the contrast medium from the image data of each of the first radiographic image and the second radiographic image, and generates a difference image in which the contrast medium is emphasized. Specifically, the controller 70 of the console 6 of the present embodiment generates image data of a difference image, in which the human body structure is suppressed and the administered contrast medium is emphasized, by subtracting image data, which is obtained by multiplying the image data (each pixel value) of the first radiographic image by a first coefficient set in advance, from image data, which is obtained by multiplying the image data (each pixel value) of the second radiographic image by a second coefficient set in advance, for each corresponding pixel. The difference image generation method of the controller 70 is not limited thereto, and a known difference image generation method can be used.

Next, the operation of the radiographic image capturing system 1 of the present embodiment will be described with reference to the accompanying diagrams. First, contrast imaging processing in the case of performing contrast imaging in the mammography apparatus 10 of the present embodiment will be described.

Figure 5:
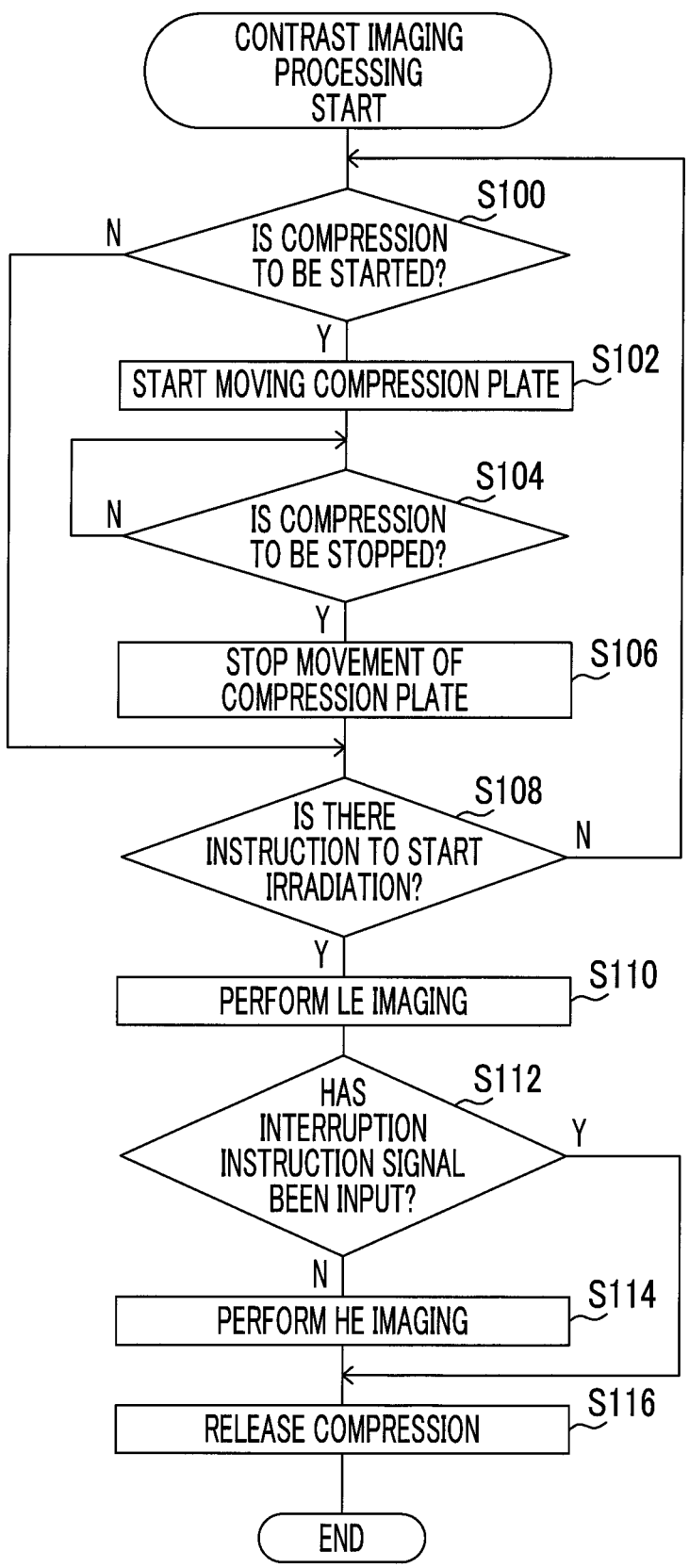
FIG. 5 is a flowchart showing an example of the flow of contrast imaging processing performed by the mammography apparatus of the first embodiment.

The mammography apparatus 10 performs the contrast imaging processing in a case where an instruction to perform contrast imaging is included in the imaging order received from the console 6. FIG. 5 shows a flowchart showing an example of the flow of the contrast imaging processing performed by the controller 60 of the mammography apparatus 10 of the present embodiment. In the mammography apparatus 10 of the present embodiment, the CPU 60A of the controller 60 executes a contrast imaging program stored in the ROM 60B, thereby performing the contrast imaging processing shown in FIG. 5.

In step S100, the controller 60 determines whether or not to start breast compression. In the radiographic image capturing system 1 of the present embodiment, in the case of performing contrast imaging, first, the user positions the breast of the subject on the imaging surface 24 of the imaging table 16 of the mammography apparatus 10 in a state in which the contrast medium is administered. In a case where the positioning is completed, in order to fix the breast by compressing the breast between the imaging table 16 and the compression plate 20 using the compression plate 20, an instruction to start compressing the breast is given by using the operation panel 66.

The determination in step S100 is negative until the instruction to start compression is given by using the operation panel 66, and the process proceeds to step S108. On the other hand, in a case where the instruction to start compression is given by using the operation panel 66, the determination in step S100 is positive, and the process proceeds to step S102.

In step S102, the controller 60 causes the compression plate driving unit 21 to start moving the compression plate 20 in a direction approaching the imaging surface 24.

In the next step S104, the controller 60 determines whether or not to stop the compression. In the present embodiment, in a case where the user desires to stop the movement of the compression plate 20, the user gives an instruction to stop the movement of the compression plate 20 through the operation panel 66. The determination in step S104 is negative until the instruction to stop the movement of the compression plate 20 is given by using the operation panel 66, and the movement of the compression plate 20 is continued. On the other hand, in a case where the instruction to stop the movement of the compression plate 20 is given by using the operation panel 66, the determination in step S104 is positive, and the process proceeds to step S106.

In step S106, the controller 60 stops the movement of the compression plate 20 by the compression plate driving unit 21.

In the next step S108, the controller 60 determines whether or not there is an instruction to start irradiation. In the present embodiment, as described above, an irradiation instruction signal for giving an instruction to emit the radiation R is output from the irradiation instruction device 50 in a case where the button 52 of the irradiation instruction device 50 is pressed by the user. The irradiation instruction signal is input to the mammography apparatus 10 through the console 6. The determination in step S108 is negative until the irradiation instruction signal is input. In a case where the irradiation instruction signal is input, the determination in step S108 is positive, and the process proceeds to step S110.

In step S110, the controller 60 performs LE imaging by emitting the radiation R having the first energy from the radiation source 29. In a case where a filter located in the irradiation field is not the Rh filter 42 (is the Cu filter 44), the controller 60 moves the Rh filter 42 and the Cu filter 44 so that the Rh filter 42 is located in the irradiation field.

The radiographic image generated by the LE imaging by the radiation detector 11 is output from the mammography apparatus 10 to the console 6. Hereinafter, the radiographic image captured by the LE imaging is referred to as a "first radiographic image".

In the next step S112, the controller 60 determines whether or not an interruption instruction signal for giving an instruction to interrupt contrast imaging, which will be described in detail later, has been input from the console 6. In a case where the interruption instruction signal is not input, the determination in step S112 is negative, and the process proceeds to step S114.

In step S114, the controller 60 performs HE imaging by emitting the radiation R having the second energy from the radiation source 29, and then the process proceeds to step S116. In addition, the controller 60 moves the Rh filter 42 and the Cu filter 44 so that the filter located in the irradiation field is changed from the Rh filter 42 to the Cu filter 44, and then emits the radiation R.

The radiographic image generated by the HE imaging by the radiation detector 11 is output from the mammography apparatus 10 to the console 6. Hereinafter, the radiographic image captured by the HE imaging is referred to as a "second radiographic image".

On the other hand, in a case where the interruption instruction signal is input, the determination in step S112 is positive, and the process proceeds to step S116.

In step S116, the controller 60 releases the compression of the breast by the compression plate 20 by moving the compression plate 20 in a direction away from the imaging surface 24 using the compression plate driving unit 21, and then ends this contrast imaging.

Next, control processing in the case of performing contrast imaging in the console 6 of the present embodiment will be described.

Figure 6:
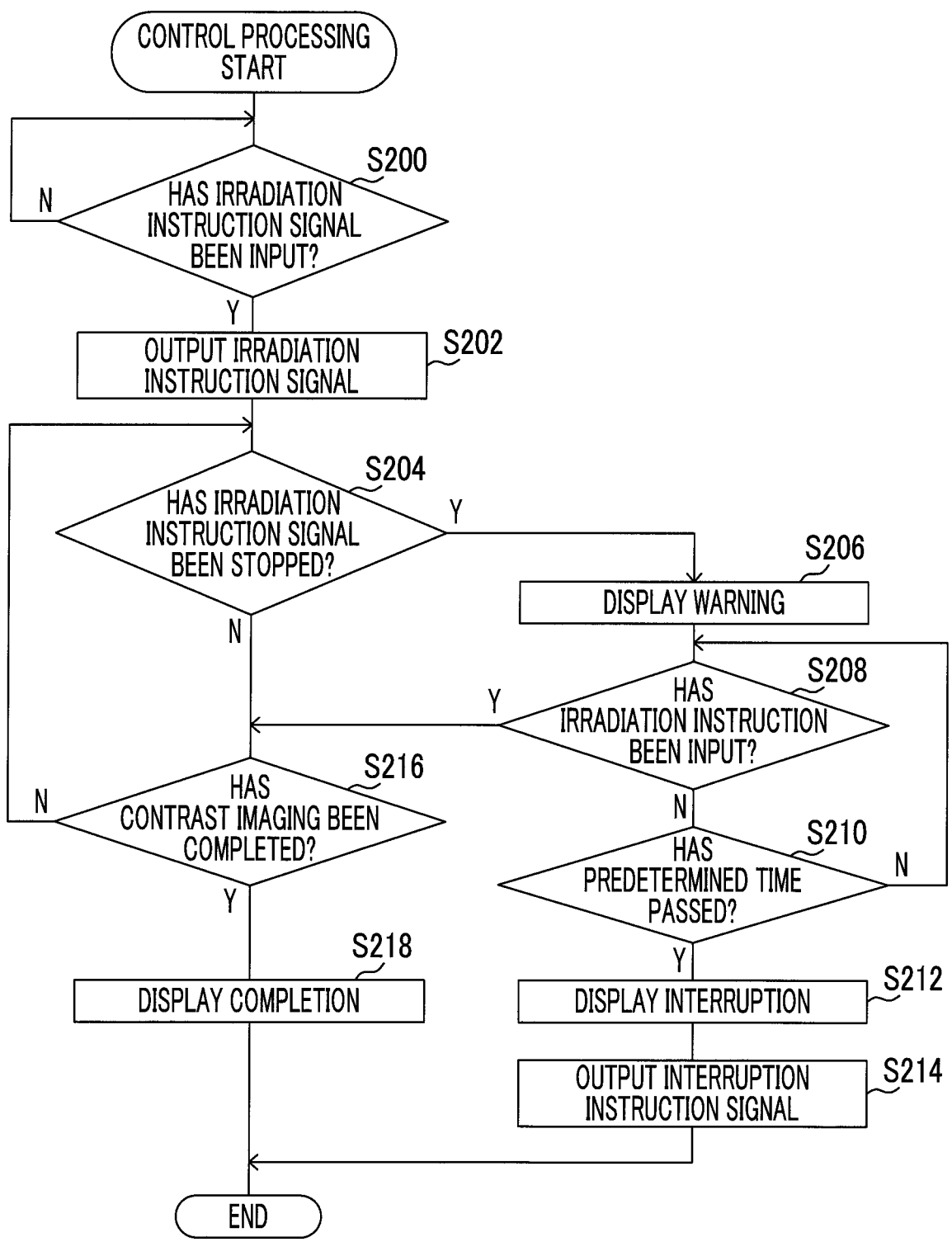
FIG. 6 is a flowchart showing an example of the flow of control processing performed by the console of the first embodiment.

In a case where the imaging order received from the RIS includes an instruction to perform contrast imaging, the console 6 transmits the received imaging order to the mammography apparatus 10 and performs control processing shown as an example in FIG. 6. FIG. 6 shows a flowchart showing an example of the flow of the control processing performed by the controller 70 of the console 6 of the present embodiment. In the console 6 of the present embodiment, the CPU 70A of the controller 70 performs the control processing shown in FIG. 6 by executing a control processing program stored in the ROM 70B, and functions as an example of a controller and a determination unit of the present disclosure.

In step S200, the controller 70 determines whether or not an irradiation instruction signal has been input from the irradiation instruction device 50. The determination in step S200 is negative until the irradiation instruction signal is input. On the other hand, in a case where the irradiation instruction signal is input, the determination in step S200 is positive, and the process proceeds to step S202.

In step S202, the controller 70 outputs the irradiation instruction signal to the mammography apparatus 10.

In the next step S204, the controller 70 determines whether or not the irradiation instruction signal input from the irradiation instruction device 50 has been stopped. In a case where the irradiation instruction signal is stopped, the determination in step S204 is positive, and the process proceeds to step S206. In the radiographic image capturing system 1 of the present embodiment, in a case where the user releases the button 52 of the irradiation instruction device 50, the irradiation instruction signal output from the irradiation instruction device 50 is stopped. In a case where the irradiation instruction signal output from the irradiation instruction device 50 is stopped while the mammography apparatus 10 is performing contrast imaging, the console 6 interrupts the contrast imaging of the mammography apparatus 10 after a predetermined time has passed.

Figure 7:
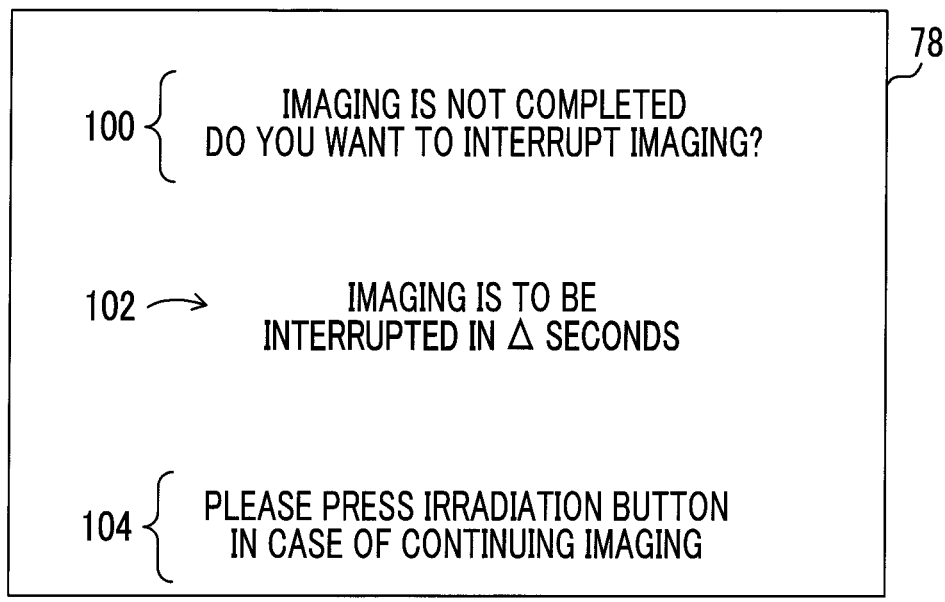
FIG. 7 is a diagram showing an example of a state in which information indicating a warning is displayed on a display unit of the console in the first embodiment.
Figure 8:
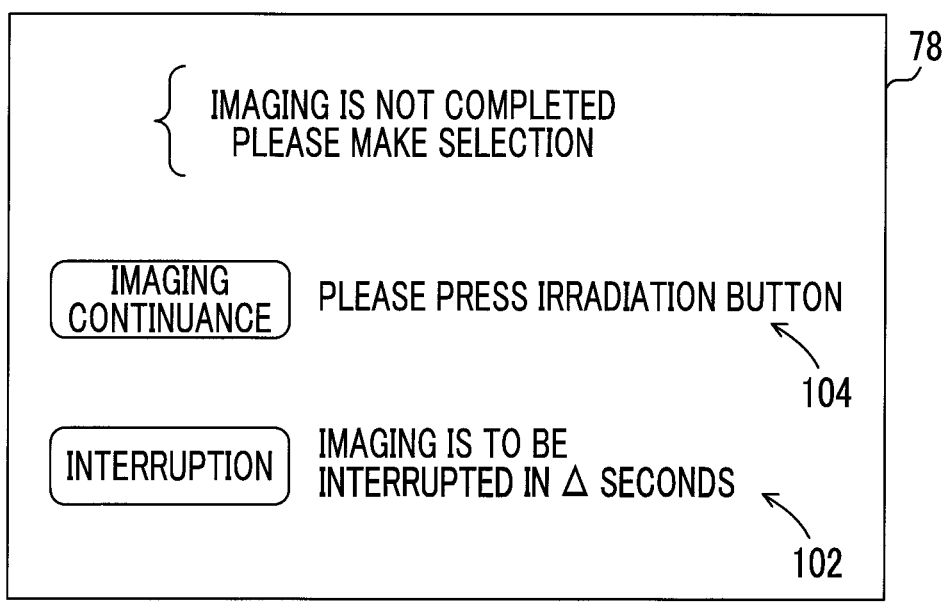
FIG. 8 is a diagram showing another example of the state in which information indicating a warning is displayed on the display unit of the console in the first embodiment.

In step S206, the controller 70 displays information, which indicates a warning that the contrast imaging is interrupted before the completion of the contrast imaging, on the display unit 78. FIG. 7 shows an example of the display of information indicating the warning displayed on the display unit 78. FIG. 8 shows another example of the display of the information indicating the warning displayed on the display unit 78. In the examples shown in FIGS. 7 and 8, a state is shown in which, in addition to information 100 indicating a warning, information 102 indicating the remaining time until interruption of contrast imaging and information 104 indicating a handling method in the case of continuing the contrast imaging without interruption are displayed on the display unit 78. The information 102 indicates the remaining time until the contrast imaging is interrupted, specifically, the remaining time until reaching a predetermined time, at which the contrast imaging is interrupted, after the irradiation instruction signal is stopped.

The user who has checked the information 104 presses the button 52 of the irradiation instruction device 50 again in a case where the contrast imaging is not interrupted. In this case, the irradiation instruction signal is input from the irradiation instruction device 50 to the console 6 again. On the other hand, in the case of interrupting the contrast imaging, the user keeps the button 52 of the irradiation instruction device 50 at it is without pressing the button 52. In this case, the irradiation instruction signal remains stopped.

In the next step S208, the controller 70 determines whether or not the irradiation instruction signal has been input. In a case where the irradiation instruction signal is input, the determination in step S208 is positive, and the process proceeds to step S216. On the other hand, in a case where the irradiation instruction signal is not input, the determination in step S208 is positive, and the process proceeds to step S210.

In step S210, the controller 70 determines whether or not a predetermined time has passed. In the present embodiment, the predetermined time can be set according to the time until the user presses the button 52 of the irradiation instruction device 50 again after the user releases the button 52 of the irradiation instruction device 50 and then checks the information 104 indicating the warning displayed on the display unit 78 of the console 6, the interval between LE imaging and HE imaging in the mammography apparatus 10, and the like.

In a case where the predetermined time has not passed, the determination in step S210 is negative, and the process returns to step S208. On the other hand, in a case where the predetermined time has passed, the determination in step S210 is positive, and the process proceeds to step S212.

Figure 9:
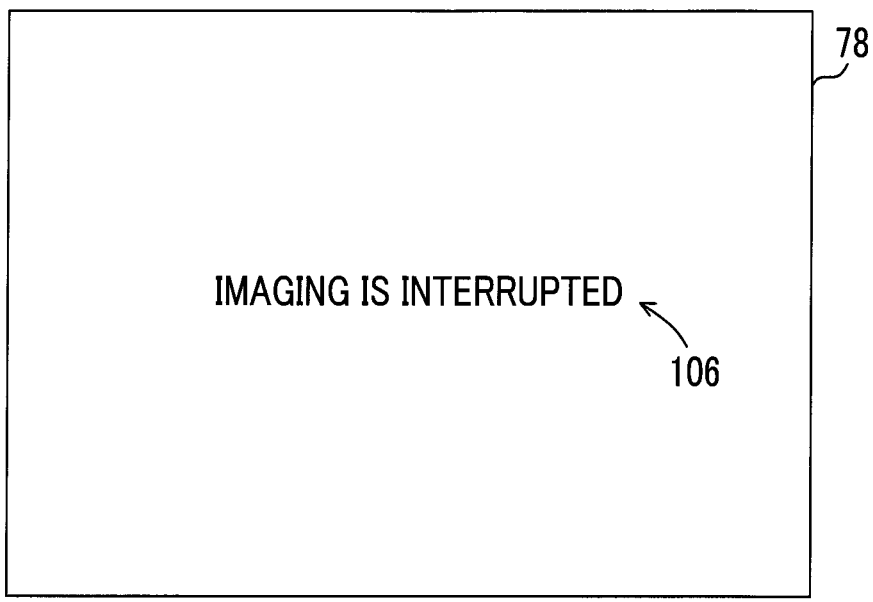
FIG. 9 is a diagram showing an example of a state in which information indicating that contrast imaging is interrupted is displayed on the display unit of the console in the first embodiment.

In step S212, the controller 70 displays information indicating that the contrast imaging is interrupted on the display unit 78. FIG. 9 shows an example of a state in which information 106 indicating that the contrast imaging is interrupted is displayed on the display unit 78.

In the next step S214, the controller 70 outputs an interruption instruction signal for interrupting the contrast imaging to the mammography apparatus 10, and then ends the control processing. In the mammography apparatus 10 to which the interruption instruction signal is input from the console 6, the contrast imaging is interrupted as described above, and the compression plate 20 is moved to release the compression of the breast.

On the other hand, in a case where the irradiation instruction signal is not stopped, the determination in step S204 is negative, and the process proceeds to step S216. In step S216, the controller 70 determines whether or not the contrast imaging has been completed. The controller 70 of the present embodiment considers that the contrast imaging has been completed in a case where image data of the second radiographic image captured by the mammography apparatus 10 in the second imaging is input from the mammography apparatus 10. Therefore, the determination in step S216 is negative until the image data of the second radiographic image is input, and the process returns to step S204. On the other hand, in a case where the image data of the second radiographic image is input, the determination in step S216 is positive, and the process proceeds to step S218.

Figure 10:
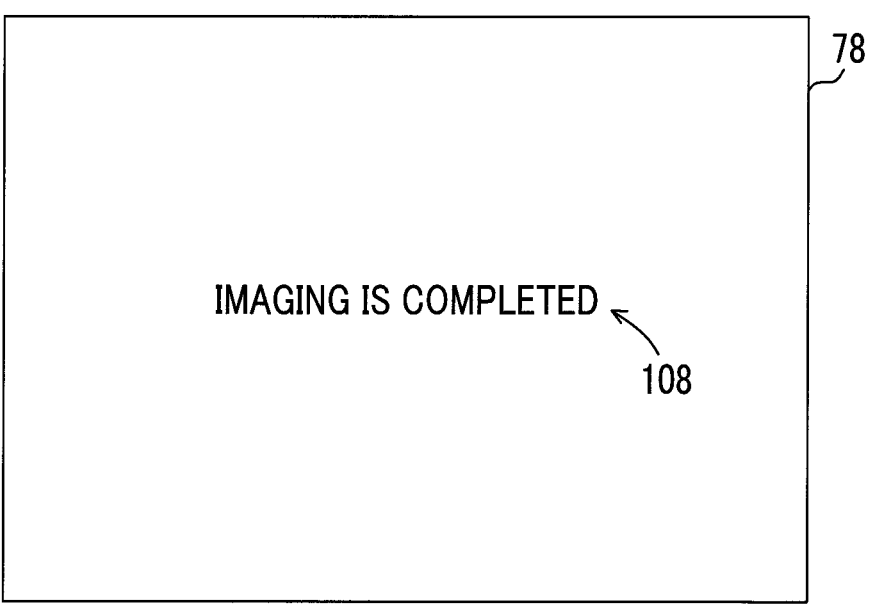
FIG. 10 is a diagram showing an example of a state in which information indicating the completion of contrast imaging is displayed on the display unit of the console in the first embodiment.

In step S218, the controller 70 displays information indicating the completion of the contrast imaging on the display unit 78, and ends this control processing. FIG. 10 shows an example of a state in which information 108 indicating the completion of contrast imaging is displayed on the display unit 78. In a case where the contrast imaging is completed, the user stops pressing the button 52 of the irradiation instruction device 50. In the radiographic image capturing system 1 of the present embodiment, the timing at which the information 108 indicating the completion of contrast imaging is displayed on the display unit 78 of the console 6 can be set as a timing at which pressing the button 52 of the irradiation instruction device 50 is stopped. Therefore, the user can easily recognize the timing at which pressing the button 52 is stopped.

As described above, in the radiographic image capturing system 1 of the present embodiment, the irradiation instruction device 50 outputs the irradiation instruction signal while the button 52 is pressed by the user. In a case where the irradiation instruction signal is input, the console 6 causes the mammography apparatus 10 to start the contrast imaging. In a case where the irradiation instruction signal is stopped during the execution of contrast imaging, the console 6 displays the information 100 indicating a warning that the contrast imaging is interrupted on the display unit 78. Then, in a case where the irradiation instruction signal is input again before a predetermined time passes after the irradiation instruction signal is stopped, the console 6 continues the contrast imaging of the mammography apparatus 10 as it is. On the other hand, in a case where the irradiation instruction signal remains stopped even though a predetermined time has passed after the irradiation instruction signal is stopped, the console 6 interrupts the contrast imaging of the mammography apparatus 10.

In the radiographic image capturing system 1 of the present embodiment, as described above, in a case where the irradiation instruction signal is stopped during the execution of contrast imaging, the console 6 displays the information 100 indicating a warning that the contrast imaging is interrupted on the display unit 78. Therefore, even in a case where the user erroneously stops pressing the button 52 of the irradiation instruction device 50, the contrast imaging can be continued without interruption.

Second Embodiment

Hereinafter, a second embodiment will be described in detail.

The overall configuration of the radiographic image capturing system 1 and the configuration of each of the console 6, the mammography apparatus 10, and the irradiation instruction device 50 are the same as those in the first embodiment, and accordingly, the description thereof will be omitted. In addition, since contrast imaging processing performed by the controller 60 of the mammography apparatus 10 is the same as the contrast imaging processing (refer to FIG. 5) performed by the controller 60 of the mammography apparatus 10 of the first embodiment, the description thereof will be omitted. In the present embodiment, since a part of control processing performed by the controller 70 of the console 6 is different from the control processing (refer to FIG. 6) performed by the controller 70 of the console 6 of the first embodiment, the different processing will be described.

Figure 11:
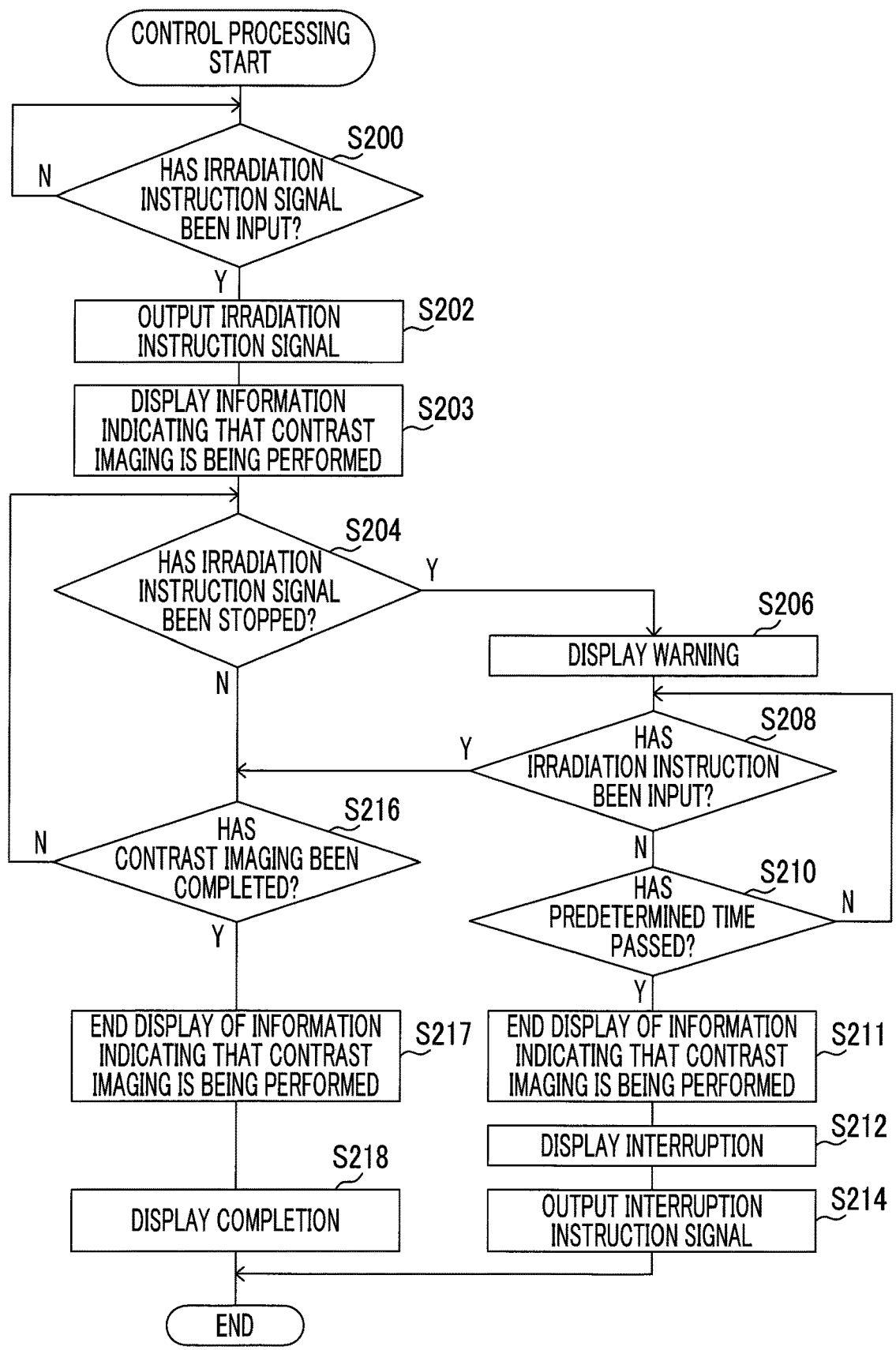
FIG. 11 is a flowchart showing an example of the flow of control processing performed by a console of a second embodiment.

FIG. 11 shows a flowchart showing an example of the flow of the control processing performed by the controller 70 of the console 6 of the present embodiment. The control processing shown in FIG. 11 is different from the control processing (refer to FIG. 6) of the first embodiment in that processing of step S203 is performed after step S202 and before step S204, processing of step S217 is performed before step S218 in a case where determination in step S216 is positive, and processing of step S211 is performed before step S212 in a case where determination in step S210 is positive.

Figure 12:
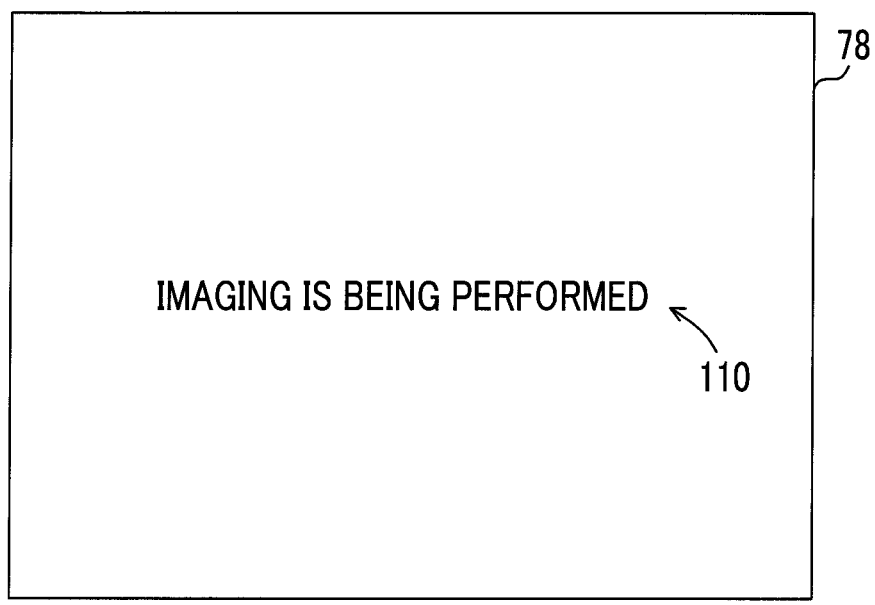
FIG. 12 is a diagram showing an example of a state in which information indicating that contrast imaging is being performed is displayed on a display unit of the console in the second embodiment.

As shown in FIG. 11, in step S203, the controller 70 displays information indicating that the contrast imaging is being performed on the display unit 78. FIG. 12 shows an example of a state in which information 110 indicating that the contrast imaging is being performed is displayed on the display unit 78. By outputting the irradiation instruction signal to the mammography apparatus 10 by the processing of step S202 as described above, the contrast imaging is started in the mammography apparatus 10. Therefore, the console 6 displays the information 110 indicating that the contrast imaging is being performed on the display unit 78.

As shown in FIG. 11, in step S211, the controller 70 ends the display of the information 110, which is displayed on the display unit 78 in the above step S203 and which indicates that the contrast imaging is being performed. As described above, the contrast imaging of the mammography apparatus 10 is interrupted in a case where a predetermined time passes after the irradiation instruction signal is stopped. Therefore, the console 6 ends the display of the information 110 indicating that the contrast imaging is being performed.

In addition, as shown in FIG. 11, in step S217, the controller 70 ends the display of the information 110, which is displayed on the display unit 78 in the above step S203 and which indicates that the contrast imaging is being performed. As described above, in a case where the contrast imaging of the mammography apparatus 10 is completed, the determination in step S216 is positive. Therefore, the console 6 ends the display of the information 110 indicating that the contrast imaging is being performed.

As described above, the console 6 of the present embodiment displays the information 110 indicating that the contrast imaging is being performed on the display unit 78 until the contrast imaging is completed or interrupted from the start of the contrast imaging in the mammography apparatus 10.

Therefore, since the user can easily recognize that the mammography apparatus 10 is performing the contrast imaging, it is possible to suppress the occurrence of a situation in which the user stops pressing the button 52 of the irradiation instruction device 50 even though the contrast imaging is not interrupted.

Third Embodiment

Hereinafter, a third embodiment will be described in detail.

The overall configuration of the radiographic image capturing system 1 and the configuration of each of the console 6, the mammography apparatus 10, and the irradiation instruction device 50 are the same as those in the first embodiment, and accordingly, the description thereof will be omitted. The controller 70 of the console 6 of the present embodiment functions as an example of a reception unit of the present disclosure.

In addition, since contrast imaging processing performed by the controller 60 of the mammography apparatus 10 is the same as the contrast imaging processing (refer to FIG. 5) performed by the controller 60 of the mammography apparatus 10 of the first embodiment, the description thereof will be omitted. In the present embodiment, since a part of control processing performed by the controller 70 of the console 6 is different from the control processing (refer to FIG. 6) performed by the controller 70 of the console 6 of the first embodiment, the different processing will be described.

Figure 13:
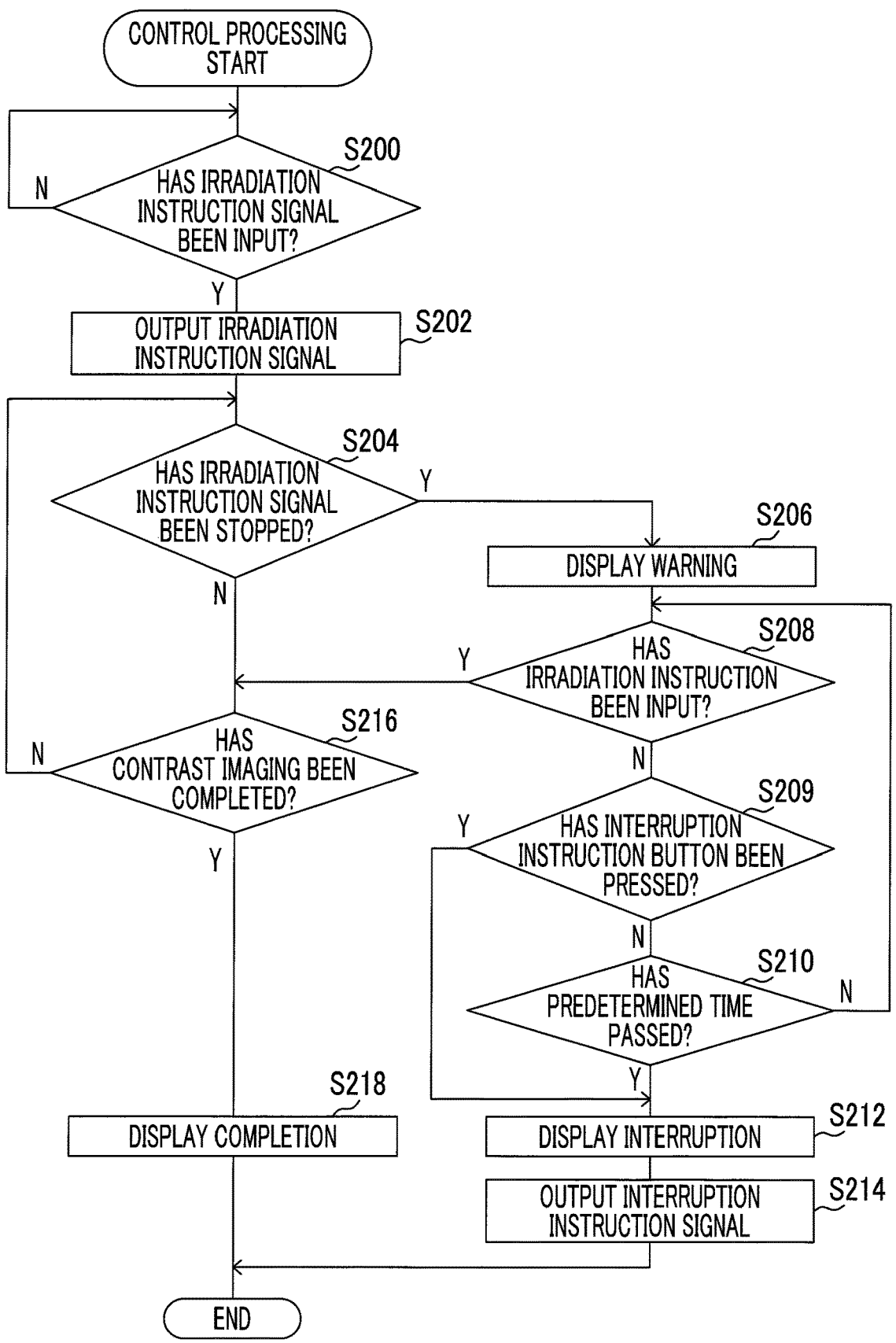
FIG. 13 is a flowchart showing an example of the flow of control processing performed by a console of a third embodiment.

FIG. 13 shows a flowchart showing an example of the flow of the control processing performed by the controller 70 of the console 6 of the present embodiment. The control processing shown in FIG. 13 is different from the control processing (refer to FIG. 6) of the first embodiment in that processing of step S209 is performed before step S210 in a case where the determination in step S208 is negative.

Figure 14:
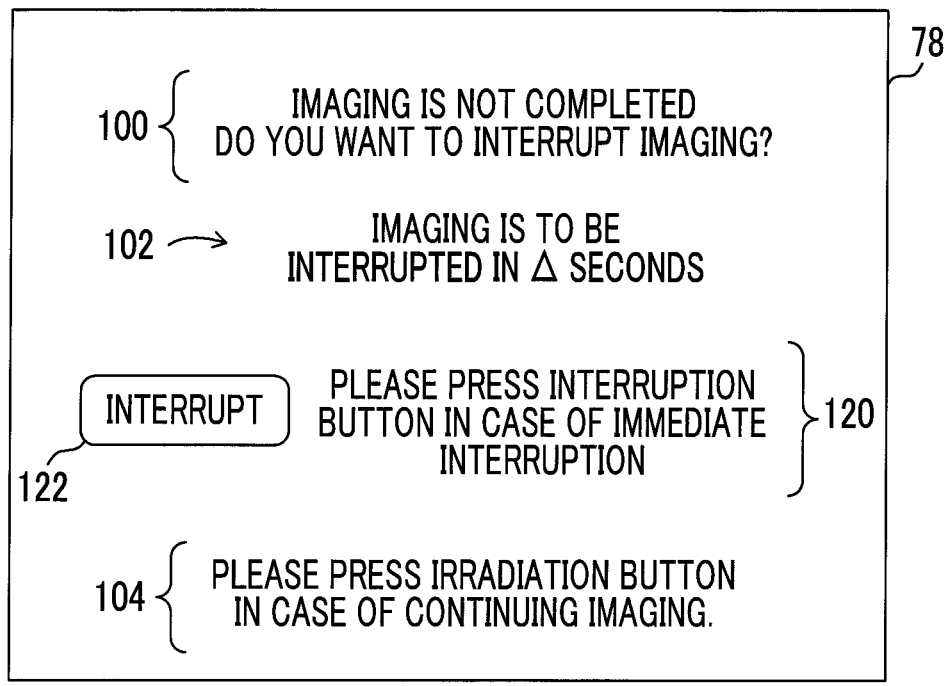
FIG. 14 is a diagram showing an example of a state in which information indicating a warning is displayed on a display unit of the console in the third embodiment.

In addition, in the present embodiment, a part of information displayed on the display unit 78 together with the information 100 indicating a warning that the contrast imaging is interrupted by the controller 70 in step S206 is different from that described with reference to FIG. 7 in the first embodiment. FIG. 14 shows an example of the display of information indicating the warning displayed on the display unit 78 in the present embodiment. In the example shown in FIG. 14, a state is shown in which, in addition to the information 100 indicating the warning, the information 102 indicating the remaining time until interruption of contrast imaging, and the information 104 indicating a handling method in the case of continuing the contrast imaging without interruption, all of which are shown in FIG. 7, information 120 indicating a handling method in the case of interruption and an interruption instruction button 122 are further displayed on the display unit 78.

In the present embodiment, the user can interrupt the contrast imaging immediately before reaching a predetermined time by operating (pressing) the interruption instruction button 122 displayed on the display unit 78 with the operation unit 82 as shown in the information 120 indicating the handling method in the case of interruption.

Therefore, as shown in FIG. 13, in step S209, the controller 70 determines whether or not the interruption instruction button 122 has been pressed by the user. In a case where the interruption instruction button 122 is not pressed, the determination in step S209 is negative, and the process proceeds to step S210. On the other hand, in a case where the interruption instruction button 122 is pressed, the determination in step S209 is positive, and the process proceeds to step S212.

As described above, in the console 6 of the present embodiment, after the user stops pressing the button 52 of the irradiation instruction device 50, the user operates the interruption instruction button 122 displayed on the display unit 78. Therefore, it is possible to interrupt the contrast imaging immediately before the predetermined time passes. In this manner, in a case where the user does not stop pressing the button 52 of the irradiation instruction device 50 by mistake but desires to interrupt the contrast imaging truly, it is possible to interrupt the contrast imaging immediately.

As described above, the radiographic image capturing system 1 of each embodiment described above comprises: the irradiation instruction device 50 that outputs an irradiation instruction signal in response to a user operation; the mammography apparatus 10 that performs contrast imaging in which a breast in a state in which a contrast medium is administered is compressed by the compression plate 20 and first imaging, in which the radiation R having the first energy is emitted from the radiation source 29 to the breast according to the irradiation instruction signal and the first radiographic image is generated by the radiation detector 11, and second imaging, in which the radiation R having the second energy different from the first energy is emitted from the radiation source 29 to the breast and the second radiographic image is generated by the radiation detector 11, are continuously performed; and the console 6 that performs control to display the information 100 indicating a predetermined warning on the display unit 78 in a case where the irradiation instruction signal is stopped before the second imaging is completed after the start of the first imaging.

In the radiographic image capturing system 1 of each of the above embodiments, as described above, in a case where the irradiation instruction signal is stopped during the execution of contrast imaging, the console 6 displays the information 100 indicating a warning that the contrast imaging is interrupted on the display unit 78. Accordingly, even in a case where the user erroneously stops pressing the button 52 of the irradiation instruction device 50, the contrast imaging can be continued without interruption.

Therefore, in the radiographic image capturing system 1 of each of the above embodiments, since re-imaging can be suppressed, it is possible to reduce the burden on the subject in the contrast imaging.

In each of the above embodiments, the form has been described in which the controller 70 of the console 6 performs processing for displaying the information 100 indicating a warning in response to the stop of the irradiation instruction signal. However, instead of the controller 70 of the console 6, other apparatuses such as the mammography apparatus 10 may perform the above processing. In addition, each process included in the contrast imaging processing performed by the controller 60 of the mammography apparatus 10 described in each of the above embodiments and each process included in the control processing performed by the console 6 may also be performed by other apparatuses.

In each of the above embodiments, the form has been described in which the information 100 indicating a warning is displayed on the display unit 78 of the console 6. However, the display content, display method, and display location of the information 100 indicating the warning are not particularly limited, and any method and location that can be easily recognized by the user who presses the button 52 of the irradiation instruction device 50 may be used. For example, display using voice is possible, or a warning may be given by blinking or lighting a light emitting diode (LED) provided in the mammography apparatus 10.

The contrast imaging processing and the control processing executed in a case where the CPU executes software (program) in each of the embodiments described above may be executed by various processors other than the CPU. As processors in this case, a programmable logic device (PLD) whose circuit configuration can be changed after manufacture, such as a field-programmable gate array (FPGA), and a dedicated electric circuit that is a processor having a dedicated circuit configuration for executing specific processing, such as an application specific integrated circuit (ASIC), are exemplified. The contrast imaging processing and the control processing may be executed by one of these various processors, or may be executed by a combination of two or more processors of the same type or different types (for example, a plurality of FPGAs and a combination of a CPU and an FPGA). More specifically, the hardware structure of these various processors is an electric circuit in which circuit elements, such as semiconductor elements, are combined.

In each of the above embodiments, the form has been described in which various programs stored in the controller 60 of the mammography apparatus 10 and the controller 70 of the console 6 are stored (installed) in advance in the ROMs (60B, 70B) of the controller 60 and the controller 70. However, the present invention is not limited thereto. The contrast imaging processing program and the control processing program may be provided in a form recorded on a recording medium, such as a compact disk read only memory (CD-ROM), a digital versatile disk read only memory (DVD-ROM), and a universal serial bus (USB) memory. Alternatively, the contrast imaging processing program and the control processing program may be downloaded from an external apparatus through a network.

In addition, the configurations, operations, and the like of the radiographic image capturing system 1, the console 6, the mammography apparatus 10, and the like described in the above embodiments are merely examples, and it is needless to say that these can be changed according to the situation without departing from the gist of the present invention. It is needless to say that the embodiments described above may be appropriately combined. The disclosure of Japanese Patent Application No. 2017-145848 filed on Jul. 27, 2017 is entirely incorporated in this specification by reference. All documents, patent applications, and technical standards described in this specification are incorporated in this specification to the same extent as in a case where the incorporation of individual documents, patent applications, and technical standards by reference is described specifically and individually.

EXPLANATION OF REFERENCES

1: radiographic image capturing system
6: console
10: mammography apparatus
11: radiation detector
11A: detector surface
12: imaging unit
14: base unit
16: imaging table
18: holding unit
20: compression plate
21: compression plate driving unit
22: support unit
24: imaging surface
26: support arm
28: radiation emission unit
29: radiation source
42: Rh filter
44: Cu filter
50: irradiation instruction device
52: button
54: I/F unit
56: gripping unit
60, 70: controller
60A, 70A: CPU
60B, 70B: ROM
60C, 70C: RAM
62, 72: storage unit
64, 74: I/F unit
66: operation panel
68: radiation source driving unit
69, 83: bus
76: display unit driving unit
78: display unit
80: operation input detection unit
82: operation unit
100, 102, 104, 106, 108, 110, 120: information
122: interruption instruction button
R: radiation

What is claimed is:

1. A radiographic image capturing system, comprising:
an instruction unit that outputs an instruction signal in a case in which a user performs an operation, and that stops outputting of the instruction signal in a case in which the user stops the operation;
a mammography apparatus that performs contrast imaging so as to compress a breast, onto which a contrast medium is administered, by a compression plate, and to continuously execute first imaging, in which radiation having a first energy is emitted from a radiation source to the breast and a first radiographic image is generated by a radiation detector, and second imaging, in which radiation having a second energy different from the first energy is emitted from the radiation source to the breast and a second radiographic image is generated by the radiation detector; and
a controller that performs control to have the mammography apparatus perform the contrast imaging in a case in which the instruction signal is received, and a period during which outputting of the instruction signal is stopped does not exceed a predetermined time, and to display information indicating a predetermined warning on a display unit prior to an interruption of contrast imaging, in a case in which the instruction signal is stopped before the second imaging is completed after start of the first imaging.

2. The radiographic image capturing system according to claim 1,
wherein the controller interrupts the contrast imaging of the mammography apparatus in a case where the stop of the instruction signal is maintained after a predetermined time has passed after displaying the information indicating the warning on the display unit.

3. The radiographic image capturing system according to claim 2,
wherein the mammography apparatus releases compression of the breast by the compression plate in a case of interrupting the contrast imaging.

4. The radiographic image capturing system according to claim 2,
wherein the information indicating the warning includes information indicating a remaining time until the contrast imaging is interrupted.

5. The radiographic image capturing system according to claim 2, further comprising:
a reception unit that receives an instruction to interrupt the contrast imaging,
wherein the controller interrupts the contrast imaging of the mammography apparatus in a case where the reception unit receives the interruption instruction.

6. The radiographic image capturing system according to claim 2,
wherein the controller causes the contrast imaging of the mammography apparatus to continue in a case where the instruction signal is output again from the instruction unit before the predetermined time passes after the instruction signal is stopped.

7. The radiographic image capturing system according to claim 1, wherein the information indicating the warning includes information indicating that the contrast imaging is interrupted.

8. The radiographic image capturing system according to claim 1,
wherein the controller displays information indicating that the contrast imaging is being performed on the display unit until the contrast imaging of the mammography apparatus is completed or interrupted from start of the contrast imaging.

9. The radiographic image capturing system according to claim 1,
wherein, in a case where the contrast imaging is completed, the controller displays information indicating the completion of the contrast imaging on the display unit.

10. A control device that controls a mammography apparatus that performs contrast imaging so as to compress a breast, onto which a contrast medium is administered, by a compression plate, and to continuously execute first imaging, in which radiation having a first energy is emitted from a radiation source to the breast according to an instruction signal output from an instruction unit in response to a user operation and a first radiographic image is generated by a radiation detector, and second imaging, in which radiation having a second energy different from the first energy is emitted from the radiation source to the breast and a second radiographic image is generated by the radiation detector, the control device comprising:
a determination unit that determines whether or not the instruction signal has been stopped, in a case in which a user stops an operation, before the second imaging is completed after start of the first imaging; and
a controller that performs control to have the mammography apparatus perform the contrast imaging in a case in which the instruction signal is received, and a period during which outputting of the instruction signal is stopped does not exceed a predetermined time, and to display information indicating a predetermined warning on a display unit prior to an interruption of contrast imaging, in a case in which the determination unit determines that the instruction signal has been stopped.

11. A control method for a mammography apparatus that performs contrast imaging so as to compress a breast, onto which a contrast medium is administered, by a compression plate, and to continuously execute first imaging, in which radiation having a first energy is emitted from a radiation source to the breast according to an instruction signal output from an instruction unit in response to a user operation and a first radiographic image is generated by a radiation detector, and second imaging, in which radiation having a second energy different from the first energy is emitted from the radiation source to the breast and a second radiographic image is generated by the radiation detector, the method comprising:
outputting the instruction signal in a case in which a user performs an operation, before the second imaging is completed after start of the first imaging;
determining whether or not the instruction signal has been stopped in a case in which the user stops the operation, before the second imaging is completed after start of the first imaging;
having the mammography apparatus perform the contrast imaging in a case in which the instruction signal is received, and a period during which outputting of the instruction signal is stopped does not exceed a predetermined time; and
displaying information indicating a predetermined warning on a display unit prior to an interruption of contrast imaging, in a case where it is determined that the instruction signal has been stopped.

12. A non-transitory computer readable medium storing a control program causing a computer to execute a process to control a mammography apparatus that performs contrast imaging so as to compress a breast, onto which a contrast medium is administered, by a compression plate, and to continuously execute first imaging, in which radiation having a first energy is emitted from a radiation source to the breast according to an instruction signal output from an instruction unit in response to a user operation and a first radiographic image is generated by a radiation detector, and second imaging, in which radiation having a second energy different from the first energy is emitted from the radiation source to the breast and a second radiographic image is generated by the radiation detector, the process comprising:
outputting the instruction signal in a case in which a user performs an operation, before the second imaging is completed after start of the first imaging;
determining whether or not the instruction signal has been stopped in a case in which the user stops the operation, before the second imaging is completed after start of the first imaging;
having the mammography apparatus perform the contrast imaging in a case in which the instruction signal is received, and a period during which outputting of the instruction signal is stopped does not exceed a predetermined time; and
displaying information indicating a predetermined warning on a display unit prior to an interruption of contrast imaging, in a case in which it is determined that the instruction signal has been stopped.

* * * * *